United States Patent [19]

De Clercq et al.

[11] 4,230,708
[45] Oct. 28, 1980

[54] THERAPEUTIC APPLICATION OF (S) -OR (RS)-9-(2, 3-DIHYDROXYPROPYL) ADENINE FOR USE AS ANTIVIRAL AGENTS

[75] Inventors: Erik De Clercq, Leuven, Belgium; Antonin Holy, Prague, Czechoslovakia

[73] Assignees: Stichting Rega V.Z.W., Leuven, Belgium; Ceskoslovenska Akademie Ved., Prague, Czechoslovakia; part interest to each

[21] Appl. No.: 952,983

[22] Filed: Oct. 20, 1978

[30] Foreign Application Priority Data

Oct. 20, 1977 [NL] Netherlands .................. 7711513

[51] Int. Cl.$^2$ .................................. A61K 31/52
[52] U.S. Cl. ......................................... 424/253
[58] Field of Search ........................... 424/253

[56] References Cited

U.S. PATENT DOCUMENTS 3,836,656  9/1974  Buzzolini ..................... 424/253

*Primary Examiner*—Jerome D. Goldberg
*Attorney, Agent, or Firm*—Brumbaugh, Graves, Donohue & Raymond

[57] ABSTRACT

The specification describes the use of S or RS 9-(2, 3-dihydroxypropyl) adenine either alone or in combination with ara-A for the treatment of virus diseases.

2 Claims, 4 Drawing Figures

THERAPEUTIC APPLICATION OF (S) -OR (RS)-9-(2, 3-DIHYDROXYPROPYL) ADENINE FOR USE AS ANTIVIRAL AGENTS

This invention relates to a novel therapeutic agent for virus diseases, and to its preparation and use.

It is known that several nucleoside compounds, i.e. compounds having a sugar moiety bound to a heterocyclic nucleus, have antiviral activities. Among them may be mentioned ara-A or 9-(beta-D-arabinofuranosyl)-adenine (compare French Pat. No. 3585 M) and ribavirin or (1-beta-D-ribofuranosyl)-1,2,4-triazole-3-carboxamide (compare Science, 177, 705, 1972, and Chemotherapy, 21, 505, 1975). Ara-A has a marked antiviral activity but only for some DNA viruses, and ribavirin has a broad-spectrum antiviral activity, i.e. an activity against several RNA and DNA viruses but its utilisation is hampered by a rather narrow safety margin.

In accordance with the invention, it has now been found that (S)-9-(2,3-dihydroxypropyl)adenine of the following formula:

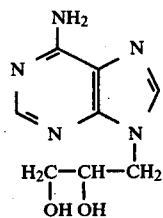

exhibits a marked broad-spectrum antiviral activity (against RNA as well as DNA viruses) and that it has a very low acute toxicity. This is surprising since it could not be expected that the substitution of a dihydroxypropyl group for a sugar moiety (when compared with ara-A) would result in any maintenance of antiviral activity. Moreover, it would not be expected that the compound of the invention, hereafter termed (S)-DHPA, would have a broad-spectrum antiviral activity since the antiviral activity of ara-A is limited only to DNA viruses. Finally, its low toxicity is surprising in view of the high toxicity of ribavirin.

It should be noted that only the D-glycero form or S-enantiomeric form of 9-(2,3-dihydroxypropyl)adenine is active and not the L-form or R-enantiomeric form. Further, the RS-form or racemic mixture is almost as effective as the S-form.

Further, it should be noted that several related compounds having another heterocyclic nucleus or another aliphatic side chain do not exhibit any antiviral activities, at least not in acceptable doses, as may appear from the experimental part of this specification. Thus, the antiviral activity of (S)-DHPA is still more surprising.

Furthermore, it should be noted that (S)-DHPA potentiates the antiviral activity of other antiviral agents, such as ara-A, and can, therefore, be used in combination with these antiviral agents.

On the basis of these findings, the invention provides a novel therapeutic composition for use in the treatment of virus diseases which comprises an effective amount of (S)-9-(2,3-dihydroxypropyl)adenine or (RS)-9-(2,3-dihydroxypropyl)adenine as an active ingredient. (S) or (RS)-9-(2,3-dihydroxypropyl)adenine can be used as the sole active ingredient or in combination with other active ingredients, such as ara-A. Furthermore, the invention provides a method of preparing such a therapeutic composition by combining (S)-9-(2,3-dihydroxypropyl)adenine or (RS)-9-(2,3-dihydroxypropyl)adenine with a pharmaceutically acceptable excipient, and a method for treatment of virus diseases, which comprises administering the aforementioned therapeutic composition to a patient suffering from a virus disease.

The process for the preparation of both the (S)-enantiomer and the racemic (RS)-form of 9-(2,3-dihydroxypropyl)adenine is known. The synthesis of these compounds is therefore no part of the present invention. Thus, according to procedure published by Holy (Collect. Czech. Chem. Commun., 40, 187, 1975), both compounds can be prepared by heating 1-O-p-tolylsulfonyl-2,3-O-isopropylidene-D- (or DL-) glycerol of the formula A

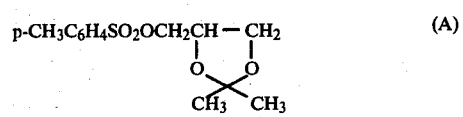

with the sodium salt of adenine in dimethylformamide solution at 100° C. and treatment of the intermediate compound with refluxing 80% acetic acid. E.g., 11.4 g (40 mmol) of compound A and 7.8 g (50 mmol) sodium salt of adenine in dimethylformamide (100 ml) is heated for 8 h at 100° C., evaporated in vacuo and the residue crystallized from methanol. The crystalline product is refluxed with 80% acetic acid for 1 h, evaporated in vacuo, codistilled with ethanol (3×50 ml) and crystallized from methanol. Yield 50–60% of (S)- or (RS)-9-(2,3-dihydroxypropyl)adenine. (S)-form: M.p. 202°–203° C., $[\alpha]_D^{25} -35.4°$ (c=1, water). (RS)-form: M.p. 207°–208° C. UV-Spectra (pH 7): $\lambda_{max}$ 260 nm, $\epsilon_{max}$ 14000, $\lambda_{min}$ 228 nm.

According to the Czechoslovak Author's certificate PV 1787-77 (RS)-9-(2,3-dihydroxypropyl)adenine can be obtained by heating of adenine with glycerol-1,2-cyclic carbonate of the formula B

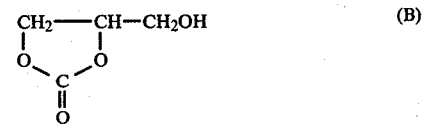

and sodium or potassium hydroxide or carbonate in dimethylformamide or 1,4-dioxane solution at 80°–140° C. E.g., a mixture of adenine (1.35 g), glycerol-1,2-cyclic carbonate (2.0 g), sodium carbonate (0.3 g) and dimethylformamide (25 ml) is refluxed for 1 h, evaporated in vacuo and the residue dissolved in 50 ml boiling water is decolorized by charcoal. After evaporation in vacuo, the residue affords on crystallization from methanol racemic (RS)-9-(2,3-dihydroxypropyl)adenine in 60–70% yield. M.p. 205°–206° C., UV-spectra (water): $\lambda_{max}$ 260 nm, $\epsilon_{max}$ 14000.

The antiviral activities of (S)-DHPA will now be described in detail. Reference is made thereby to the drawings, wherein.

The antiviral activity of (S)-DHPA was explored in a variety of cell cultures and with a variety of DNA and RNA viruses such as listed in Table 1. The cells of each cell culture were inoculated with a certain virus in a dose of about 100 $CCID_{50}$, that is about 100 times the dose needed to infect 50% of the cells. One hour after inoculation, (S)-DHPA was added in varying doses from zero to 40 μg/ml and sometimes to more than 200 μg/ml. For each virus-cell system, the $ID_{50}$ of (S)-DHPA, that is the dose of (S)-DHPA needed to suppress the cytopathic effect of the virus by 50%, was determined. This cytopathic effect (CPE) was measured in the untreated virus-infected cell cultures [(S)-DHPA dose 0] and recorded as soon as it reached completion (according to the method described by L. J. Rosenthal and I. L. Shechmaister, in "Tissue Culture", page 510, Academic Press, New York, 1973). The results of these experiments are shown in Table 1.

It appears from Table 1, that several DNA and RNA viruses including vaccinia, herpes simplex (types 1 and 2), measles and vesicular stomatitis virus, were inhibited by (S)-DHPA. Other viruses such as polio, Coxsackie and Sindbis virus were not affected.

That the inhibitory effects of (S)-DHPA on virus-induced cytopathogenicity actually reflected an inhibition of virus multiplication, was ascertained by measuring virus growth in human skin fibroblast (HSF) cultures which had been inoculated with vesicular stomatitis virus (VSV) and subsequently exposed to (S)-DHPA. In these experiments, confluent monolayers of HSF cells in plastic petri dishes were inoculated with vesicular stomatitis virus (4.5 $log_{10}$ $CCID_{50}$/0.5 ml/petri dish) for 1 h at 37° C. and, immediately thereafter, exposed to (S)-DHPA (100 μg/ml). The cell cultures were then incubated for varying times at 37° C. At the end of the incubation period, the cells were frozen at −70° C., and the cell homogenates were assayed for virus content by plaque formation in mouse L-929 fibroblast cultures. This method is well-known. Each plaque is produced by a virus having infected a cell, multiplied within the cell and burst the cell. As the cell monolayers are overlaid by a gel-like medium (e.g. agar) the viruses released upon the destruction of the cell can only invade neighbour cells, resulting in the formation of a zone of cell destruction, called plaque. The number of plaques is equivalent to the virus content. The results are presented graphically in FIG. 1, where PFU means Plaque Formation Units.

Figure 1:
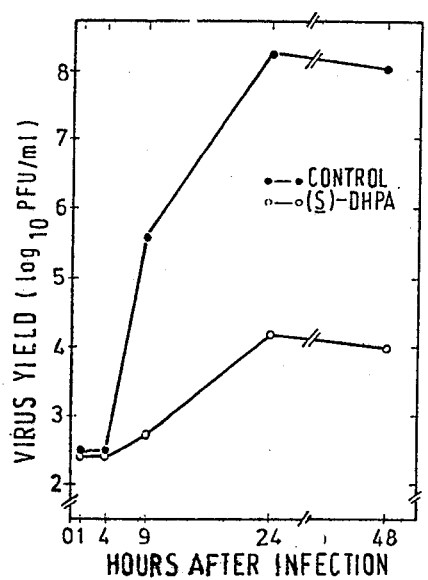
FIG. 1 is a graphical representation showing the effect of (S)-DHPA on human skin fibroblast cultures inoculated with vesicular stomatitis virus.

It appears from FIG. 1 that 100 μg/ml of (S)-DHPA caused a dramatic decrease of virus titer, as compared with the control culture where no (S)-DHPA was added. This decrease amounted to approximately 4 $log_{10}$ for the virus yields measured at 24 and 48 h after infection.

TABLE 1

| Antiviral activity of (S)-DHPA in cell cultures | | |
|---|---|---|
| Virus | Cell culture* | $ID_{50}$ (μg/ml) |
| DNA viruses | | |
| Vaccinia | PRK | 10–20 |
| Vaccinia | HSF | 10–20 |
| Herpes simplex-1 strain KOS | PRK | 10 |
| Herpes simplex-1 strain KOS | HSF | 20 |
| Herpes simplex-2 strain 333 | PRK | 4–10 |
| Herpes simplex-2 strain 333 | HSF | 7–20 |
| RNA viruses | | |
| Vesicular stomatitis | PRK | 7–10 |
| Vesicular stomatitis | HSF | 2–7 |
| Vesicular stomatitis | HeLa | >200 |
| Polio-1 | HSF | >200 |
| Polio-1 | HeLa | >200 |
| Coxsackie B-4 | HeLa | >200 |
| Coxsackie B-4 | Vero | >200 |
| Measles | Vero | 4–40 |
| Sindbis | BHK | >200 |

*Abbreviations:
PRK, primary rabbit kidney;
HSF, human skin fibroblast;
Vero, a continuous cell line of green monkey kidney cells;
BHK, a continuous cell line of baby hamster kidney cells.

The potential in vivo activity of (S)-DHPA was assessed in mice infected with vesicular stomatitis virus (VSV) according to the method described in J. Gen. Virol., 5, 359 (1969) and J. Clin. Invest., 49, 1565 (1970). Twenty days old female NMRI mice (average weight 15 g) were inoculated intranasally with vesicular stomatitis virus (2.5 $log_{10}$ $CCID_{50}$/0.01 ml/mouse). Thereupon, they were repeatedly injected intraperitoneally with (S)-DHPA at a dose of 2 mg/mouse (about 133 mg/kg) at 1 h and 1, 2, 3 and 4 days after the virus infection. Deaths were recorded daily and the cumulative mortality was determined. The results for 14 consecutive days are graphically presented in FIG. 2. No deaths were noted beyond the 14th day after infection.

Figure 2:
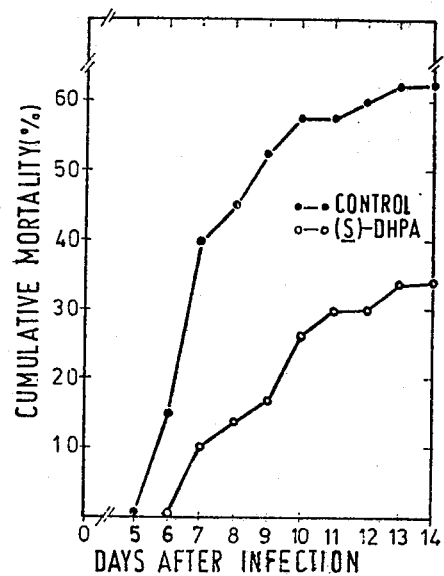
FIG. 2 is a graphical representation showing the effect of (S)-DHPA in vivo in mice inoculated intranasally with vesicular stomatitis virus.

It appears from FIG. 2 that the repeated doses of (S)-DHPA at 2 mg/mouse brought about a significant increase in the final number of surviving mice: 67% for the (S)-DHPA-treated mice as compared to 37.5% for the control group. If the numbers of survivors were compared at 9 days after infection, the difference between the test group and the control group was also significant.

The experiments of FIG. 2 were repeated with different (S)-DHPA levels. Repeated doses of 0.08 mg/mouse of (S)-DHPA (about 5.4 mg/kg) did not confer protection, whereas repeated doses of 0.4 mg/mouse (about 27 mg/kg) causes a slight protection (final number of surviving mice 55%, as compared to 37.5% for the control group).

Experiments for assessing the acute toxicity of (S)-DHPA have also been carried out in mice but a $LD_{50}$ value (dose lethal for 50% of the mice) could not yet been determined, due to the fact that all mice survived (without any sign of illness) after they had received (S)-DHPA doses up to 1000 mg/kg/day for 3 to 5 days.

From the foregoing experiments, it is evident that (S)-DHPA is a useful therapeutic agent for virus diseases.

In addition to (S)-DHPA, various related substances have been examined in the virus-cell systems of Table 1 in which (S)-DHPA exhibited a marked antiviral activity: VSV/PRK, vaccinia/PRK and herpes simplex-1 (KOS)/PRK. Only the (S)-enantiomer of DHPA proved active. The (R)-enantiomer, (R)-DHPA, was not. The racemic mixture, (RS)-DHPA, was almost as effective as the (S)-enantiomer. Whereas (S)-DHPA and (RS)-DHPA inhibited the cytopathic effects of VSV, vaccinia and herpes simplex-1 (KOS) at a level of about 10 μg/ml, the following congeners of (S)-DHPA did not demonstrate an antiviral activity at 100 μg/ml (the highest level tested): S-9-(2,3-dihydroxypropyl)-hypoxanthine, RS-9-(2-hydroxypropyl)adenine, 9-(2-hydroxyethyl)adenine, 9-(2-aminoethyl)adenine, 9-(β-DL-alanyl)-adenine, S-9-(3,4-dihydroxybutyl)adenine, RS-9-(3,4-dihydroxybutyl)-adenine, RS-threo-9-(2,3,4-trihydroxybutyl)adenine, RS-9-(3,5-dihydroxypentyl)adenine, S-1-(2,3-dihydroxypropyl)thymine, R-1-(2,3-dihydroxypropyl)-thymine, S-3-(2,3-dihydroxypropyl)thymine, S-1-(3,4-dihydroxybutyl)-racil, RS-1-(3,5-dihydroxypentyl)uracil, S-1-(2,3-dihydroxypropyl)uracil, 9-(3-hydroxypropyl)adenine and 2-(9-adeninyl)-propane-1,3-diol.

In the therapy of virus diseases, (S)-DHPA may be used as such and also in the form of its racemic mixture (the RS-form). Further, it may be used in combination with other antiviral substances such as ara-A. There is, in fact, circumstantial evidence for a synergism in the antiviral activities of (S)-DHPA and ara-A.

(S)-DHPA was found to be a strong inhibitor of adenosine deaminase. Adenosine deaminase is an enzyme that is ubiquitous in cells, tissues and biological fluids. It deaminates the aforementioned ara-A to its metabolite ara-Hx [9-(beta-D-arabinofuranosyl)hypoxanthine] which is less active as an antiviral agent than ara-A (compare Ann. N.Y. Acad. Sci., 284, 60, 1977). Unlike ara-A, (S)-DHPA did not serve as a substrate for the adenosine deaminase of extracts of bacterial cells (Escherichia coli, Salmonella typhimurium) or extracts of mammalian cells (primary rabbit kidney cells). However, (S)-DHPA strongly inhibited the deamination of ara-A by adenosine deaminase, extracted from calf intestinal mucose. The latter enzyme preparation was a Calbiochem product.

Figure 3:
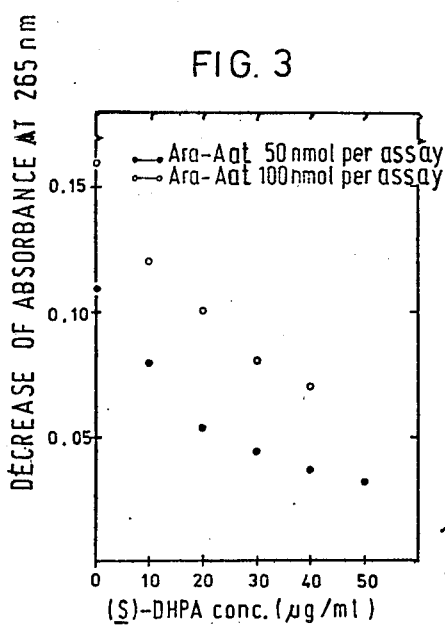
FIG. 3 is a graphical representatio showing the inhibitory effect of (S)-DHPA on deamination of ara-A by adenosinedeaminase of calf intestinal mucosa.
Figure 4:
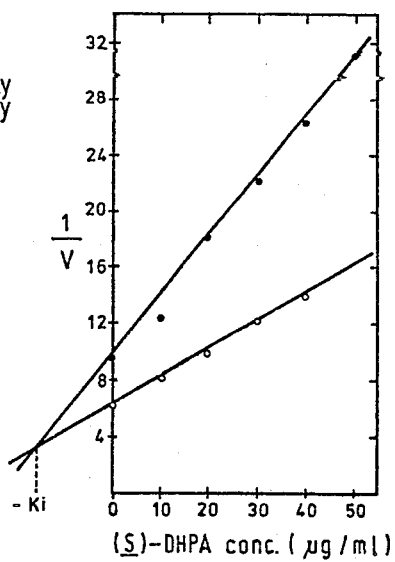
FIG. 4 is a graphical representation of the same data as in FIG. 3 but with reciprocal plotting on the ordinate.

FIG. 3 is a graphical representation showing the inhibitory effect of (S)-DHPA on deamination of ara-A by adenosine deaminase of calf intestinal mucosa. Deamination of ara-A was measured according to the method of Kalckar (compare J. Biol. Chem., 167, 461, 1972), modified by Trams and Lauter (compare Biochem. J., 152, 681, 1975). The extent of deamination is equivalent to the decrease of absorbance at λ (wavelength)=265 nm. The decrease in absorbance at 265 nm was 0.11 if 50 nmol of ara-A were used, and was 0.16 if 100 nmol of ara-A were used (FIG. 3A). In the presence of (S)-DHPA, the deamination of ara-A (as reflected by the absorbance decrease) was inhibited proportionally to the concentration of (S)-DHPA. FIG. 4 represents a reciprocal plot of the data presented in FIG. 3.

Adenosine deaminase inhibitors are known to potentiate the antiviral activity of ara-A. A typical example of such adenosine deaminase inhibitor is (R)-3-(2-deoxy-beta-D-erythro-pentofuranosyl)-3,6,7,8-tetrahydroimidazo-(4,5-d)-(1,3)-diazepin-8-ol, referred to as to CO-V or CO-vidarabine (compare Ann. N.Y. Acad. Sci., 284, 9 and 284, 60, 1977).

(S)-DHPA markedly potentiated the antiviral activity of ara-A. The synergism in the antiviral activities of (S)-DHPA and ara-A was determined in PRK (primary rabbit kidney) cultures which had been inoculated with vaccinia virus. In these experiments, confluent monolayers of PRK cells in plastic petri dishes were inoculated with vaccinia virus (4.5 log$_{10}$ CCID$_{50}$/0.5 ml/petri dish) for 1 h at 37° C. and, immediately thereafter, exposed to either (S)-DHPA alone or ara-A alone or combinations of (S)-DHPA and ara-A. Both compounds were used at various concentrations (1, 3, 10, 30 or 100 μg/ml). The cell cultures were then incubated for varying times at 37° C. At the end of the incubation period, the cells were frozen at −70° C., and the cell homogenates were assayed for virus content by plaque formation in PRK cell cultures, according to the plaque formation procedure described above for vesicular stomatitis virus in mouse L-929 fibroblast cultures. The results of a representative experiment are shown in Table 2.

It appears from Table 2 that a combination of (S)-DHPA (30 μg/ml) and ara-A (3 μg/ml) effected a much greater reduction in virus titer than did either (S)-DHPA or ara-A when used individually. Hence, (S)-DHPA may be considered to enhance the antiviral activity of ara-A. This enhancement is most probably due to the inhibitory effect of (S)-DHPA on the deamination of ara-A by adenosine deaminase.

Pharmaceutical compositions comprising (S)-DHPA, or its racemic mixture (RS)-DHPA, as an active ingredient may take the form of powders, suspensions, solutions, emulsions as well as ointments and pastes and may be used for parenteral (intravenous, intradermal, intramuscular, intrathecal, . . .) injections, oral, rectal, intravaginal and intranasal administration or topical application (e.g. to lesions of skin, mucosa and eye). These compositions may be prepared by combining the active ingredient(s) with pharmaceutically acceptable excipients which are normally used for this purpose. These excipients may comprise aqueous or non-aqueous solvents, stabilisers, suspenders, dispersers, wetting agents and the like and will be known to the pharmaceutical skilled in the art. Further, the composition may comprise any suitable additives like polyethyleneglycols, and, if necessary, dyestuffs, perfumes and the like.

TABLE 2

Synergism in the antiviral activites of (S)-DHPA and ara-A in primary rabbit kidney (PRK) cell cultures infected with vaccinia virus

| Treatment | Virus yield (log$_{10}$ PFU/ml) Days after infection | | |
|---|---|---|---|
| | 1 | 2 | 3 |
| (1) Control (infected, untreated) | 3.6 | 5.0 | 5.3 |
| (2) (S)-DHPA at 30 μg/ml | 3.6 | 4.9 | 5.4 |
| (3) Ara-A at 3 μg/ml | 2.1 | 4.0 | 5.0 |
| (4) Combined treatment (2) and (3) | 2.0 | 1.8 | 2.1 |

The pharmaceutical compositions will contain at least 0.1% by weight of the active ingredient. The actual concentration will depend on the disease and on the chosen route of administration. In general, this concentration will be comprised between 0.1% and 100%.

A particular advantage of (RS)-DHPA and (S)-DHPA is their remarkable stability which renders possible the thermic sterilization of the neutral, and weakly acid or weakly alkaline solutions. In pure form their stability is practically unlimited. The costs of production of (RS)-DHPA and (S)-DHPA are significantly lower than the costs of production of other antiviral drugs such as ara-A or ribavirin.

What we claim is:

1. A method for the treatment of viral diseases which comprises administering a therapeutically effective amount of a compound selected from the group consisting of (S)-9-(2,3-dihydroxypropyl)adenine and (RS)-9-(2,3-dihydroxypropyl)adenine to a patient suffering from a viral disease.

2. The method described in claim 1 wherein the virus is selected from the group consisting of vaccinia, herpes simplex, measles and vesicular stomatitis.

* * * * *

UNITED STATES PATENT AND TRADEMARK OFFICE
CERTIFICATE OF CORRECTION

PATENT NO. : 4,230,708
DATED : October 28, 1980
INVENTOR(S) : De Clercq et al.

It is certified that error appears in the above—identified patent and that said Letters Patent is hereby corrected as shown below:

First page, Item [30], after "Oct. 20, 1977 [NL] Netherlands ...............7711513" add --Oct. 20, 1977 Czechoslovakia ..............6839-77--;
Column 5, line 33, "mucose" should read --mucosa--.

Signed and Sealed this

Twenty-fourth Day of March 1981

[SEAL]

Attest:

RENE D. TEGTMEYER

Attesting Officer     Acting Commissioner of Patents and Trademarks